United States Patent [19]

Wood et al.

[11] Patent Number: 5,441,043
[45] Date of Patent: Aug. 15, 1995

[54] VIDEO LAPAROSCOPE WITH MODULAR VIDEO CONNECTOR AND DUAL LOW-WATTAGE LIGHT SOURCES

[75] Inventors: Robert J. Wood, Syracuse; Michael J. Pileski, Skaneateles; Gregory E. Pasik, Auburn, all of N.Y.

[73] Assignee: Welch Allyn, Inc., Skaneateles Falls, N.Y.

[21] Appl. No.: 944,221

[22] Filed: Sep. 11, 1992

[51] Int. Cl.$^6$ .............................................. A61B 1/06
[52] U.S. Cl. ........................................ 600/109; 348/75; 600/182
[58] Field of Search .......................... 128/4, 6, 8–10; 358/98; 385/115–117; 362/32, 227, 234, 267; 439/577, 191; 359/821, 367

[56] References Cited

U.S. PATENT DOCUMENTS

| | | | |
|---|---|---|---|
| 3,453,440 | 7/1969 | Muir et al. | 385/117 X |
| 4,048,486 | 9/1977 | Kriege | 385/117 X |
| 4,216,767 | 8/1980 | Aoshiro | 128/6 |
| 4,539,586 | 9/1985 | Danna et al. | 358/98 |
| 4,590,923 | 5/1986 | Watanabe | 128/6 |
| 4,604,992 | 8/1986 | Sato | 128/6 |
| 4,729,018 | 3/1988 | Watanabe et al. | 358/98 |
| 4,834,071 | 5/1989 | Hosoi et al. | 128/6 |
| 4,844,071 | 7/1989 | Chen et al. | 128/6 |
| 4,919,621 | 4/1990 | Ams | 128/6 X |
| 4,998,182 | 3/1991 | Krauter et al. | 128/6 X |
| 5,010,876 | 4/1991 | Henley et al. | 128/6 |
| 5,124,838 | 6/1992 | Forkey et al. | 359/821 X |

FOREIGN PATENT DOCUMENTS 3928492  7/1990 Germany .................. 128/6

Primary Examiner—Richard J. Apley
Assistant Examiner—John P. Leubecker
Attorney, Agent, or Firm—Harris Beach & Wilcox

[57] ABSTRACT

A laparoscope is constructed with a plug-in module containing video processing circuitry and coupled through a flexible umbilical to a rigid or partly rigid insertion tube that contains a miniature video camera. A fiber optic bundle for illumination has a bifurcated proximal end with two portions each terminating in respective sleeves that project from the module. The sleeve project from the module. The sleeves position the illumination bundle portions at the focussed spot of light produced by respective low-power metal halide discharge lamps. A rotary vane shutter is servo controlled to limit the amount of light entering the fiber optic bundle so that the monitor video picture is kept at a constant level. The metal sleeve for the fiber optic bundle ends serve as grounding elements, and are coupled by a grounding pigtail within the module to a ground conductor in the umbilical. A test opening with a threaded plug serves as a pressure test port.

3 Claims, 5 Drawing Sheets

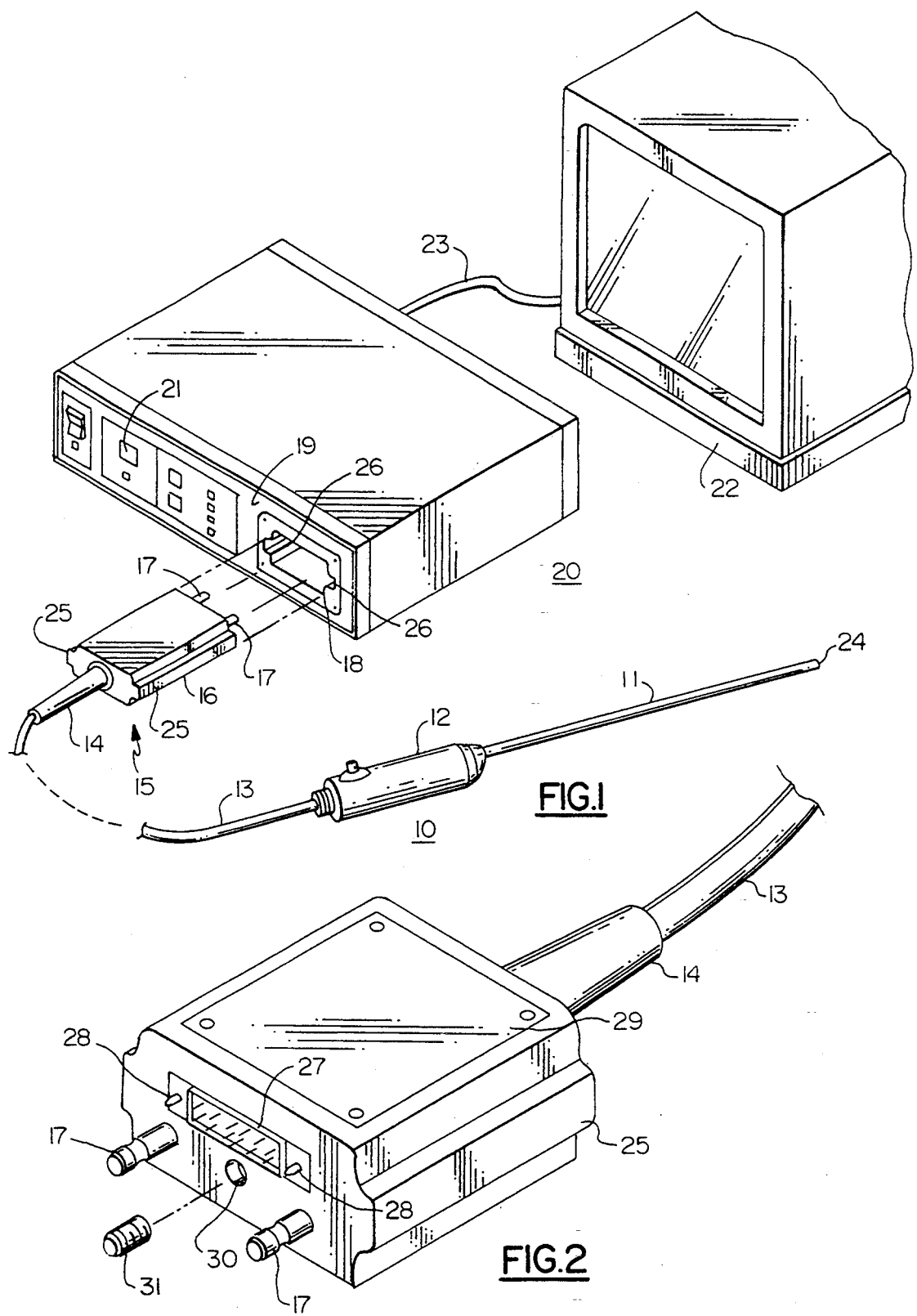

VIDEO LAPAROSCOPE WITH MODULAR VIDEO CONNECTOR AND DUAL LOW-WATTAGE LIGHT SOURCES

BACKGROUND OF THE INVENTION

This invention relates to borescope or endoscope of the type in which a miniature video camera is mounted at a distal viewing head of an elongated insertion tube. The invention is more particularly concerned with an improved laparoscope in which illumination for the miniature video camera is supplied from a low-wattage but high-efficiency lamp and thence through a light conduit to the tip of the laparoscope probe tube.

Recently, the need and preference for less invasive surgical techniques has increased the interest in the use of video instruments for surgical applications, and in video-based procedures with minimal intervention in the patient. An example of a minimally invasive video instrument is a laparoscope for performing surgery in the abdominal cavity, where the instrument is inserted through a small incision. Other probes are provided for diagnosis of medical conditions in the colon or in the gastro-enteric tract. Small probes can also be used in eye surgery. Further examples are found in industrial probes, i.e., borescopes, for inspection of equipment such as boilers or steam generators, or jet engine rotors where non-destructive penetration of the equipment is necessary. In each case the tissues or parts to be investigated may be quite sensitive to heat; thus if infrared or heat is produced with the light from the instrument's light box, inspection can injure or damage the target.

It is also desirable for the laparoscope to operate at low power consumption rates, for example, so that the unit can be constructed compactly and of light weight, and also so that the laparoscope can be made battery powered and portable, e.g., for veterinary purposes.

However, until now suitable illumination was possible only with high wattage, high pressure xenon arc lamps. These produce a large amount of waste heat and their energy cannot be focussed down onto a small spot to enter a fiber optic bundle or other light conduit. The heat is not only wasted but it can also be dangerous, as numerous cases of abdominal burns and surgical drape ignitions have been reported.

A video laparoscope with a light source based on small, low-power metal halide discharge lamp is described in copending patent application Ser. No. 07/780,762, filed Oct. 22, 1991, now U.S. Pat. No. 5,331,950, and having a common assignee. As described in that patent application, a laparoscope or other similar probe has a miniature video camera that incorporates a miniature electronic imager and a lens assembly which are disposed either at the distal tip or at a proximal end of an insertion tube. For insertion tubes of about 5 mm or larger, the camera can be distally mounted. For very slim insertion tubes, the camera can be proximally mounted, with a relay lens system being contained in the insertion tube. The insertion tube can be rigid or can have its tip portion articulatable. The small video camera can be incorporated in an add-on camera attachment for laparascopes having a proximal viewing port.

Disposing the camera at the distal tip of the laparoscope insertion tube reduces the amount of focussing and relay lenses to be carried in the tube. This means less light is lost in the lens system, so the amount of optical fiber bundle needed for illumination, is reduced which also permits the insertion tube to be made smaller.

The insertion tube proximal end is coupled through a flexible cable or umbilical to a connector module that plugs into a socket in a processor unit. A video cable that extends through the insertion tube and umbilical has terminals in the connector module that supply the video signal from the miniature camera to electronic circuitry in the processor, which supplies a suitable signal to a full color or monochrome monitor. An image of a target area, such as a tissue within a patient's body cavity, can be viewed on the monitor.

Also within the processor is a high illuminance, but low-wattage light source in the form of one or more metal halide discharge lamps. These can preferably be of the type described in Copending Patent Application Ser. Nos. 07/484,166, filed Feb. 23, 1990, now U.S. Pat. No. 5,144,201; 07/636,742, 07/636,743, and 07/636,744, each filed Dec. 31, 1990, now U.S. Pat. Nos. 5,117,154, 5,083,059, 5,138,228, respectively, and which have an assignee in common herewith. The lamp typically operates at a power of about 20 watts dc, and has an efficacy of at least 35 lumens per watt. The light produced, which can be controlled by the selection of salts employed, the dosage of mercury, and mechanical structure of the lamps, has an emission spectrum in the visible band, with very little radiation produced in the infrared band. Also, the arc gap of this lamp is small, which produces a small spot of light when focused onto the fiber optic bundle used for illumination. The small spot size allows almost all the light energy to be directed into the proximal end of a very small fiber bundle. The smaller illumination bundle permits the insertion tube to be made much smaller than was previously possible while still delivering plenty of light to the target area. Also, because small optical fiber bundles can be used, the probe can incorporate redundant optical fiber bundles, which can each be associated with a respective light source. Moreover, because the lamp operates at low power (e.g. 20 watts), producing limited infrared radiation, and with virtually all the light being focused onto the fiber optic bundle, the light source can be made much more compact, and the lamp power supply can be much smaller. The light incident on the target consists substantially only of visible light, with very little radiant heat. This permits the operator to view and examine tissues for extended intervals without danger of tissue damage or the ignition of surgical drapes.

OBJECTS AND SUMMARY OF THE INVENTION

It is an object of this invention to provide an improved laparoscope that avoids the problems of the prior art.

It is another object to provide a laparoscope which has a self-contained plug-in video module containing the electronics for operating and delivering a video signal based on an image signal from the miniature video imager in the insertion tube.

It is a further object of the invention to provide a laparoscope in which there are dual light sources and in which the illumination fiber bundle is bifurcated at its proximal end and receives illumination from both light sources.

It is yet another object to provide an attenuator or shutter system that is motor-driven based on the strength of the video signal so that the amount of illumination is automatically increased for increased target distances to keep the picture level substantially constant.

It is a related object to provide the laparoscope shutter system so that there is no noticeable change in picture brightness during an operation, notwithstanding changing target distances or possible failure of one of the light sources.

In accordance with an aspect of this invention, a laparoscope or similar probe has a miniature video camera associated with the insertion tube. The camera incorporates a miniature electronic imager and a lens assembly. A fiber optic bundle carries light for illuminating the target and emits light from the distal end of the probe.

The laparoscope has a plug-in module containing the required video processing electronics within a sealed housing. The electronics receives power from a connector mounted on the housing, sends to the camera suitable control and synchronizing signals and receives and processes image signals that represent the image of the target. From the electronics contained in the module, a video signal is provided to output terminals on the connector. The video signal can be directly connected to a suitable video monitor to provide a picture display of the target as viewed by the miniature camera. The illumination fiber optic bundle is preferably bifurcated so that it can receive light from two separate light sources. The bundle is divided into two portions which extend proximally from the proximal face of the module. These are supported in projecting metal sleeves which serve to locate the ends of the fiber bundle portion at the foci of the light sources.

The module fits insertably into a socket on a power and light unit. There is a power supply that provides power for the video circuity to a mating connector within the socket, so that power is supplied to the connector on the module and also brings off the video signal when the module is positioned in the socket.

Within the casing or cabinet of the power and light unit are a pair of light sources, each including a low-wattage (e.g. 20 w.) metal halide discharge lamp, an ellipsoidal reflector arranged with the associated lamp at a first focus to concentrate a spot of light at a second focus, and a suitable electrical ballast. The plug-in module positions the two fiber-optic bundle portions at the respective second foci so that the light focused there is concentrated onto the optical fibers. A rotary vane-type servo-controlled shutter selectively covers or exposes the ends of the respective fiber optic bundle portions to a degree as determined by the video signal intensity. This permits the illumination to vary to compensate for movement of the target, as may occur for reasons such as breathing or other unavoidable movement, thus to keep the picture level constant. The intensity of the light falling on the target will vary inversely with the square of the distance from the tip of the probe to the target, but the shutter vane is profiled to account for this. That is, the radius of the vane, from its axis of rotation to the edge that meets the location of the focussed spot, varies as a function of rotation angle, so that the amount of focal spot left unobstructed is proportional to the square of the angle of rotation. In this way, the rotation of the shutter vane is more or less linear with respect to movement of the target toward and away from the probe tip.

The use of dual light sources provides immediate back-up in the case of failure of one of the two lamps. Sufficient illumination is provided from the remaining lamp to complete the surgical procedure, and it is not necessary to interrupt the surgery to replace the lamp. However, prior to the next surgical procedure, the small lamps can be replaced quickly and without difficulty.

The above and many other objects, features, and advantages of this invention will become apparent to those skilled in the art from the ensuing description of an embodiment of this invention, to be read in conjunction with the accompanying Drawing.

BRIEF DESCRIPTION OF THE DRAWING

FIG. 1 is a perspective view of a laparoscope according to one embodiment of this invention.

FIG. 2 is a perspective view of a video processor module according to this embodiment of the invention.

DETAILED DESCRIPTION OF THE PREFERRED EMBODIMENT

Figure 3:
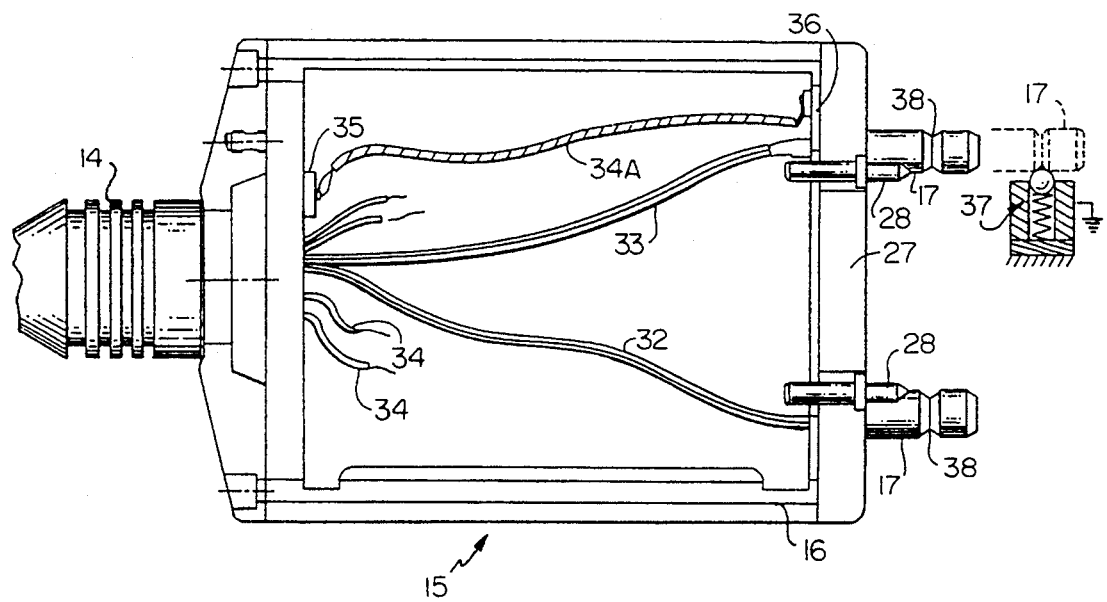
FIGS. 3 and 4 are top plan views of the video processor module showing progressive stages of assembly.

With reference to the Drawing, and initially to FIG. 1, a laparoscope 10 according to one embodiment of the present invention has an elongated, narrow insertion tube 11 having a distal tip and a control handle 12 located at its proximal end. The insertion tube can be entirely rigid, or can be rigid with the distal tip thereof being articulatable. Wires, cables, and fiber optic bundles pass from the distal tip through the insertion tube 11 and handle 12 and from there through a flexible tubular umbilical 13. The umbilical 13 is joined by a strain relief 14 to a sealed plug-in processing module 15. The module 15 has a sealed casing or housing 16 with protruding tubes or sleeves 17 that project from its proximal end. The processor module 15 serves as a connector module and plugs into a socket 18 on the front panel 19 of the cabinet of an associated light and power unit 20. The front panel 19 has associated controls and displays 21, which will be discussed later. A video monitor 22, which can be a color or black and white CRT, or can possibly be a projecting screen device or an LCD monitor, is coupled by a suitable cable 23 to the unit 20. The latter has a suitable wiring harness (70 FIG. 9) therein to connect the monitor 22 to the module 15. A miniature video camera 24 is contained in the distal tip of the insertion tube 11.

Projecting ribs 25 on the side wall of the casing 16 serve as keys for fitting into mating recesses 26 in the sides of the socket 18. The ribs are positioned somewhat asymmetrically so that the module 15 cannot be inadvertently installed upside down.

As shown in FIG. 2, there is a multi-pin electrical connector 27 disposed on the proximal wall of the module 15. This connector 27 includes several pins to bring power into the module and other pins which deliver a processed video signal that can be carried by the wiring harness and the cable 23 to the monitor 22. There are also a pair of locating pins or studs 28 disposed one on each side of the connector 27. These serve to locate or position the connector within the socket 18 when the processor module 15 is installed into the socket.

A pressure test opening 30 is here shown with a threaded plug 31 which is removably inserted therein. This opening or aperture 30 is disposed between the positions of the tubes or sleeves 17 and serves to permit pressure testing after assembly of the module.

As shown in FIG. 3, in this case, a fiber optic bundle for carrying illumination to the distal end of the insertion tube 11 has a bifurcated, proximal end disposed in the module 15. That is, the bundle is divided into a left branch 32 and a right branch 33. The two branches 32 and 33 are disposed in respective ones of the tubular sleeves 17 the sleeves 17 serve to position the proximal ends of each of the two fiber optic bundle branches 32 and 33 in position to receive light from a respective light source.

Also shown here are signal and control wires 34 which extend from the module 15, through the umbilical 13 and the insertion tube 11, to the camera 24. Two grounding straps or pigtails 34A unites a ground conductor 35 in the umbilical to a grounding plate 36 disposed on the proximal side of the housing, and which is in electrical contact with each of the two sleeves 17.

Also shown here there is a retaining detent 37 within the unit 20 and which is electrically connected to chassis ground within the light and power unit 20, and which mechanically engages an annular recess 38 in the respective sleeve 17. This both couples the ground of the module 15 to the chassis ground of the unit 20, and also positions the ends of the fiber optic branches 32 and 37 accurately with respect to light sources to be described later.

Figure 4:
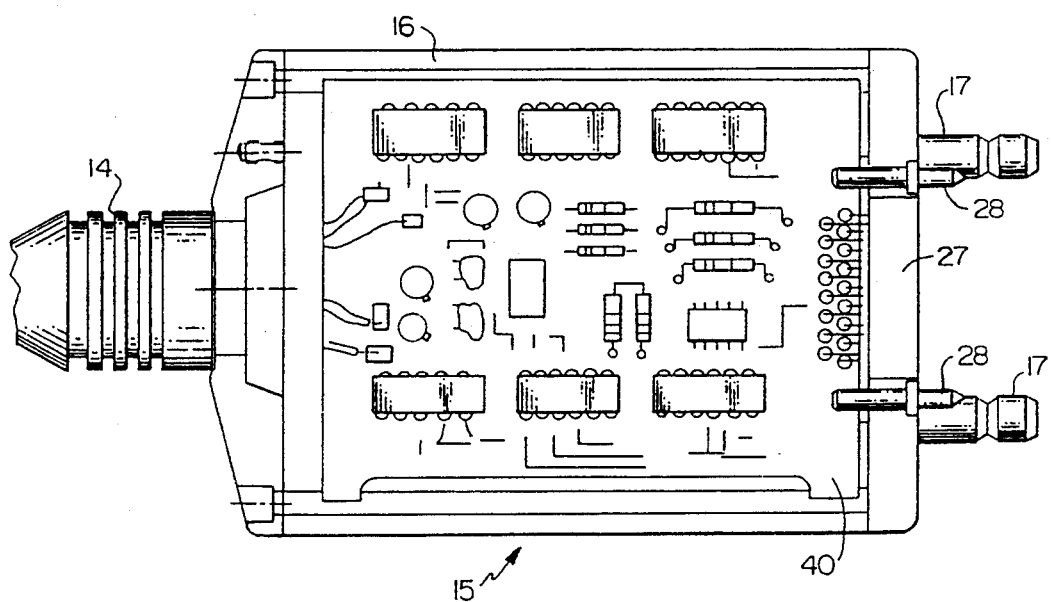

As shown in FIG. 4, one or more printed circuit boards 40 disposed within the module housing 16 contains electronics which derive power from certain ones of the terminals of the connector 27, and provide a processed video signal to other terminals of this connector 27.

The video processing circuitry also provides synchronizing and control signals over the conductors 34 to the miniature camera 24. The circuitry on the board or boards 40 receives the image signal from the camera, and processes the same to produce a suitable video signal in a desired format, e.g. NTSC, PAL, etc, so that it can be applied directly to the video monitor 22. With this arrangement, each video camera 24 is matched with its own video circuitry contained within the module 15. This means that each laparoscope is entirely modular, that is, completely interchangeable so that modular laparascopes 10 of different types can be employed using a single light and power unit 20. Also, any individual laparoscope 10 can be used with any of various similar units 20.

The laparoscope 10 is entirely sealed, and can be completely immersed in ethylene oxide or another sterilization agent for sterilization between uses.

The laparoscope 10 can be easily pressure tested by removing the threaded plug 31, and then applying pressure through the associated aperture. A traceable gas can be used, if desired, to test for leaks. After testing, dry nitrogen or another dry inert gas at a slight overpressure i.e., exceeding one atmosphere can be injected into the module 15 before replacing the plug 30 to seal the module.

Figure 5:
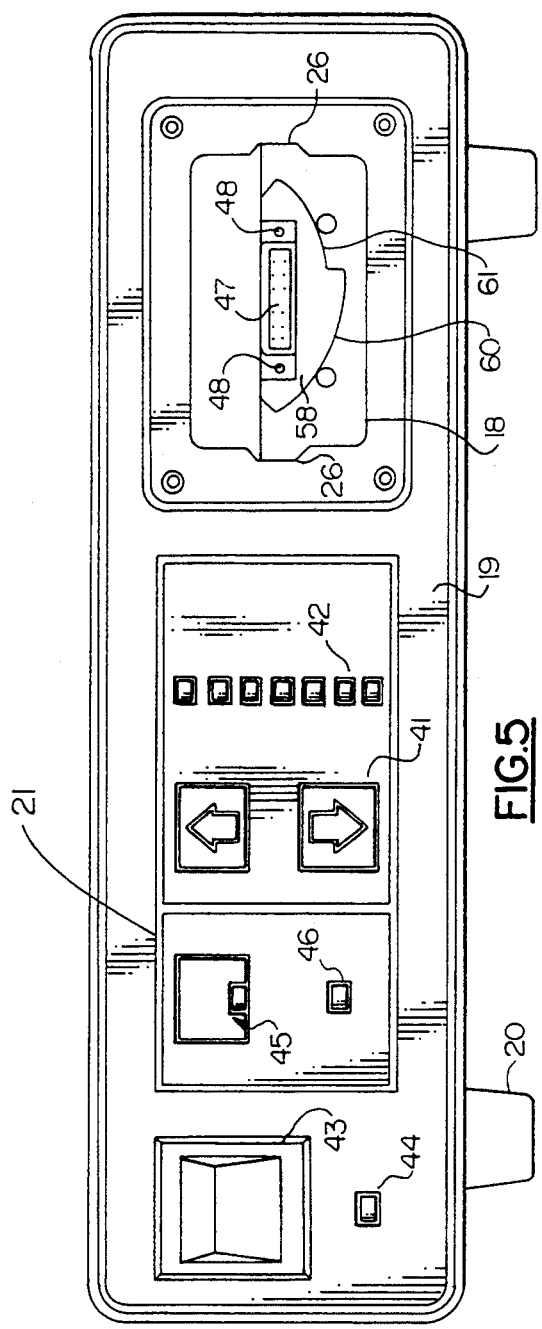
FIG. 5 is a front view of a light and power unit of this invention.

In FIG. 5, the front panel 19 of the unit 20 is shown with the light controls 21, which includes a pair of picture-brightness keys 41 and an array of level indicator LEDs 42. An on/off switch 43 is provided together with a power-on indicator LED 44. Also there is a lamp-on/standby switch 45 and a lamp service indicator LED 46. The indicator LED 46 lights when lamp failure is sensed to be imminent, based on a pattern of changing voltage or current consumption within either of the lamps within the unit 20.

The socket 18 is depicted here on the right-hand side of the panel 19. Shown within the socket is a mating electrical connector 47 which couples with the connector 27 on the module 15 when the module is plugged into the socket 18. Receptacles 48 are shown on either side of the connector 47 to receive the locating pins 28 on the module 15.

There are also receptacles 49 within the socket 18 for locating the two sleeves 17 with their respective fiber optic bundle branches, to position same at the focussed spots of light in the respective light sources.

Figure 7:
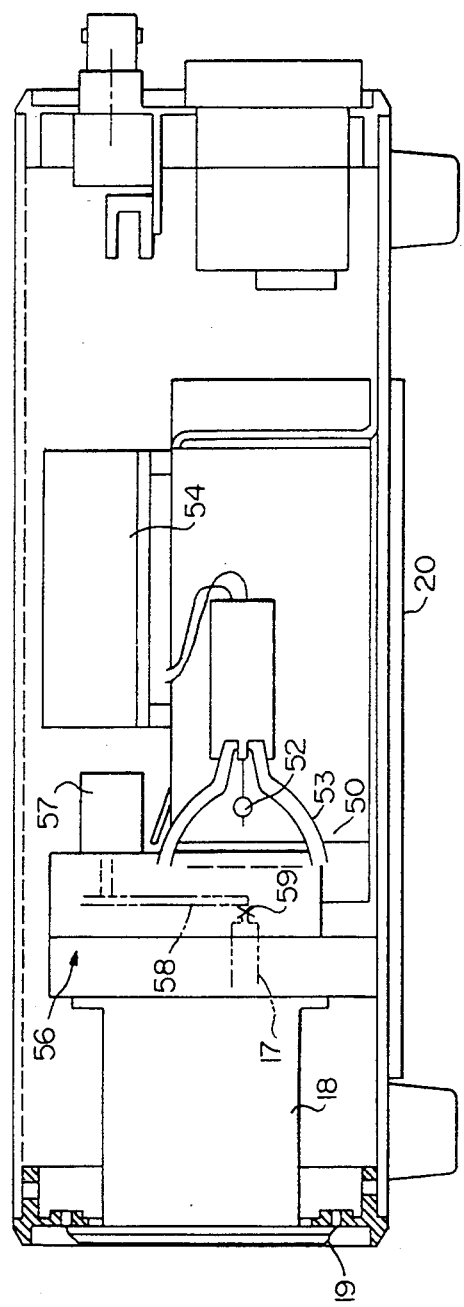
FIGS. 6 and 7 are a top plan view and an elevation of the light and power unit.
Figure 6:
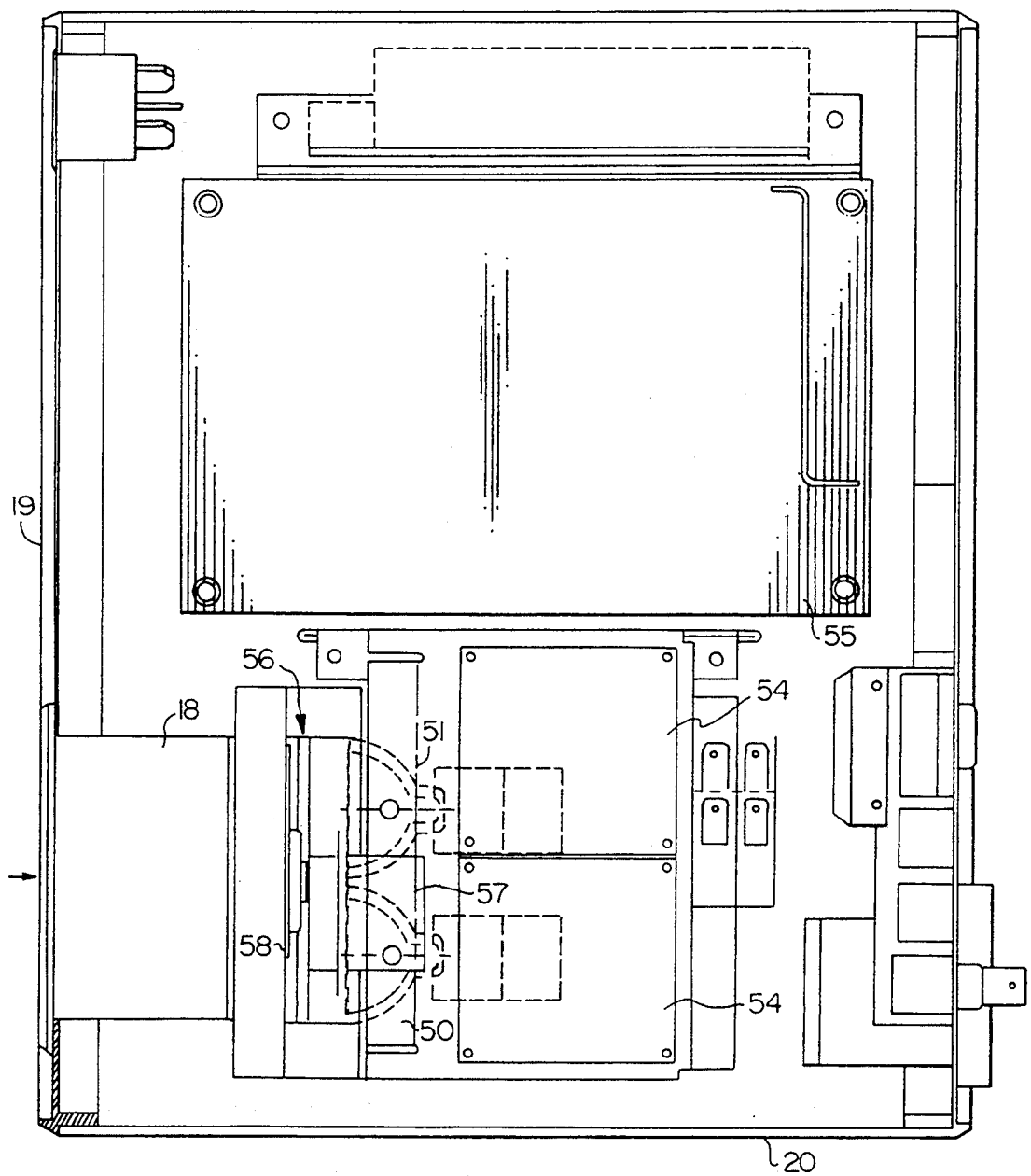

As shown in FIGS. 6 and 7, within the cabinet of the unit 20 and located behind the socket 18, there are first and second lamp assemblies 50 and 51. Each of these includes a low power metal halide discharge lamp 52 and an elliptical reflector 53, with the associated lamp 52 positioned at a first focus of the reflector. Positioned above the lamp and reflector is an associated ballast 54, i.e., a power supply for the lamp. Situated to the left of the two lamp assemblies 50 and 51 is a power supply 55, which provides appropriate electrical current to the lamp ballasts 54, and also provides the various required dc levels, through the coupler 47, to the electrical circuitry within the module 15.

The discharge lamps 52 are low-wattage units (e.g. 20 watts) containing suitable halide salts so that they emit white light, i.e., comprised of red, green and blue wavelengths, but do not produce appreciable amounts of infrared radiation. The lamps have a very small arc gap so as to constitute a point source, whereby the reflected spot at the second focus 59 is quite small.

The lamps 52 and reflectors 53 of the two lamp assemblies 50 and 51 are modularized, so that they can be quickly unplugged from their respective ballasts and replaced when necessary, gaining access to the lamp assemblies through a bottom panel (not shown) of the cabinet of the light and power unit 20.

Figure 8:
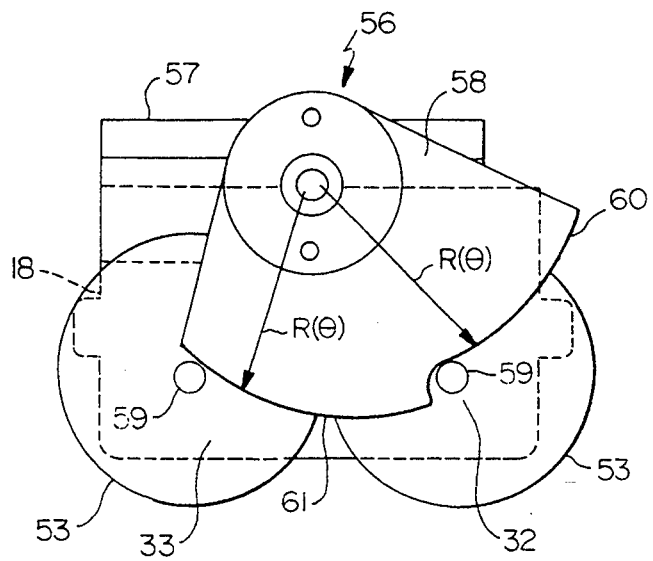
FIG. 8 is a front view of a servo shutter vane employed in this embodiment of the invention.

A light control shutter assembly 56, shown with reference to FIG. 8, includes a stepper motor 57 which controllably rotates a rotary vane 58 that is positioned beyond the reflectors and adjacent the second foci 59 of thereof. The rotary vane 58 is disposed transverse to the optical axes of the lamp assemblies and has vane edges 60 and 61 both of similar curvature, which intercept a controllable portion of the light emitted by the lamp assemblies 50 and 51. As the vane 58 is rotated, the edges 60, 61 obstruct a selected fraction of the light before it reaches the proximal end of the fiber optic bundle branches 32, 33, which are positioned, in the respective sleeves 17, at or adjacent to these second foci 59.

Because the lamps 52 have an extremely small arc gap, the light at the second focus 59 of each reflector 53 has a spot size of about 0.2 to 0.3 mm, which approximates the size of the associated fiber optic bundle branch. The rotary vane 58 selectively obstructs or covers the portion of the respective fiber optic bundle from the incident light, and thereby controls the amount of illumination carried by the fiber optic bundle. In this manner, the illumination of the target in advance of the camera 24 is regulated, so that the picture level on the monitor 22 is maintained constant.

For laparoscopes and other probes of this type the level of the illumination falling on the target drops off as the square of the distance between the target and the distal tip of the insertion tube 11. Thus, with the normal breathing of the patient, motion within the body cavity during the operation can cause significant variations in picture level. Also, other movement of the probe can occur during various procedures, which also affects the picture level. With this in mind, the shutter is constructed so that the movement of the vane 58 is substantially linear for changes in the probe to target distance. This facilitates the achievement of even picture levels during the operation.

In this embodiment, the profile of the vane 58 is selected to vary the radius $R(\theta)$ as a function of rotation angle varies so that the amount of the focused light spot reaching the respective fiber optic branch 32 or 33 is proportional to the square of the rotation angle $\theta$. That is, the percent of the optical fiber bundles that are uncovered is related to the square of the rotation angle $\theta$ of the vane 58.

Figure 9:
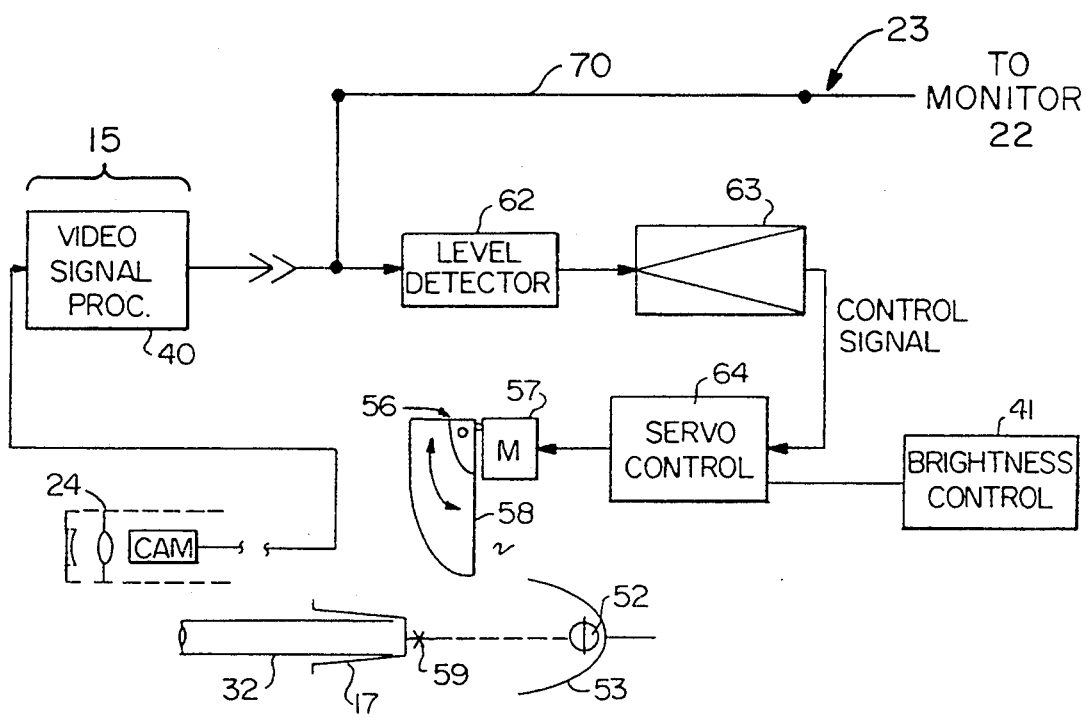
FIG. 9 is a schematic block diagram of the servo control shutter of this embodiment.

The circuitry for regulating the shutter assembly 56 is described with reference to the schematic of FIG. 9. As shown here, the output of the lamp 52, as focussed by the reflector 53, is regulated by the rotary vane 58 just as the light reaches the position of the respective fiber optic branch 32 within the sleeve 17. The light carried by the optical fibers illuminates a target, which results in a corresponding image signal being produced by the camera 24. The signal then generated by the video processor 40 will have a signal level, over some portion of the image, which is determined by the level of illumination of the target. This signal level is sensed by a level detector 62, indicating the average video signal strength at the target. The output signal from the level detector 62 is fed to a conditioning element such as an amplifier and low pass filter, to provide a control signal to a servo control circuit 64 that actuates the servo motor 67. The brightness control 41, which was mentioned earlier in discussion of FIG. 5, permits adjustment of bias level so that the surgeon or technician can adjust the picture brightness to a desired level.

Changes in the brightness level of the video signal will automatically cause rotation of the vane 58 to increase or decrease the amount of light to keep the video picture brightness level constant. Also, if one of the first and second lamp assemblies 50, 51 should fail, the servo motor 57 will automatically rotate the vane 56 to open to admit more light, to the extent possible, to restore the illumination level. This feature permits a surgeon to complete an operation procedure even in the event of a lamp failure.

While this invention has been described in detail with respect to a selected embodiment, it should be understood that the invention is not limited to that precise embodiment. Instead, many modifications and variations would present themselves to those of skill in the art without departing from the scope and spirit of this invention, as defined in the appended claims.

What is claimed is:

1. A video laparoscope system which comprises an elongated insertion tube which includes a lens assembly for focussing light which enters a distal end of the insertion tube onto a miniature video imager which produces an image signal that represents a target located distally of the insertion tube; a video processor module connected by an umbilical to said insertion tube and including a sealed housing, video processing circuitry within the housing and receiving power from terminals of an electrical connector on said housing and providing control and synchronizing signals to said video imager and processing the image signals therefrom to provide to output terminals of said electrical connector a video signal to be supplied to a video monitor to produce a picture of said target; the video signal having a signal strength that depends on brightness of illumination of said target; a fiber optic light conduit having a bifurcated proximal end with two branches each projecting proximally from said module at a respective one of two locations thereon, and extending distally from said module to pass through said umbilical and said insertion tube to the distal end of the insertion tube from which light carried in said bundle is incident upon said target to illuminate same; and a light and power unit including a cabinet which has a socket into which said video processor module is removably inserted, a power supply in said cabinet providing suitable electrical power to a mating electrical connector in said socket which contacts the electrical connector on said processor module; and a pair of light sources within the cabinet each providing illumination onto a respective one of the branches of said fiber optic conduit at one of said locations, such that in the case of failure of one of said light sources the remaining light source will continue to provide uninterrupted illumination of said target; further comprising a servo-controlled shutter having a movable vane with respective vane positions disposed in a plane transverse to the optical axes of each light source such that the illumination from each light source is concurrently obstructed, substantially to the same degree to control the amount of illumination passing through the fiber optic bundle and illuminating said target; a servo motor controlling the position of said movable vane; and a control circuit input with the signal strength of said video signal for controlling the position of the vane based on the signal strength of the video signal, such that in the event of a loss of one of said pair of light sources, the servo motor automatically moves said vane to increases the illumination provided from the other of the light sources.

2. The video laparoscope according to claim 1, wherein said servo controlled shutter vane is a rotary vane with said respective blade portions having edges which each vary in radius from an axis of rotation thereof.

3. The video laparoscope according to claim 2, wherein said radius varies as a function of angle of rotation of the vane such that the amount of illumination left unobstructed is proportional to the square of the angle of rotation.

* * * * *